Figure 1:
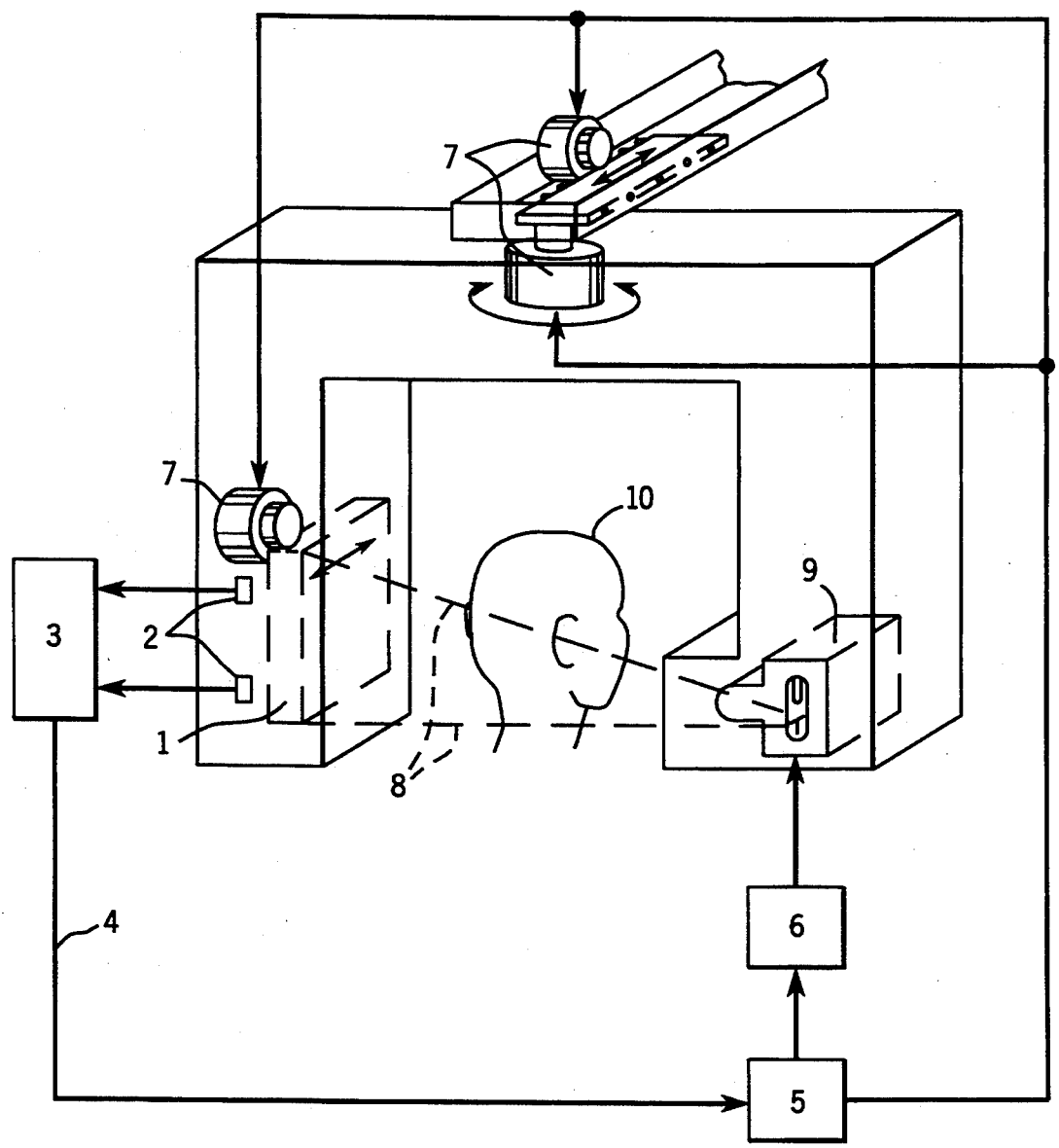

United States Patent [19]
Järvenin

[11] Patent Number: 5,425,065
[45] Date of Patent: Jun. 13, 1995

[54] AUTOMATIC EXPOSURE APPARATUS FOR PANORAMIC X-RAY EQUIPMENT

[75] Inventor: Erkki Järvenin, Palojoki, Finland

[73] Assignee: Instrumentarium Corp.- Imaging Division, Finland

[21] Appl. No.: 88,662

[22] Filed: Jul. 6, 1993

Related U.S. Application Data

[63] Continuation-in-part of Ser. No. 931,834, Aug. 18, 1992, abandoned.

[30] Foreign Application Priority Data

Aug. 19, 1991 [FI] Finland ................................ 913897

[51] Int. Cl.⁶ .................................................. A61B 6/14
[52] U.S. Cl. ........................................ 378/40; 378/39
[58] Field of Search ............................... 378/38, 39, 40

[56] References Cited

U.S. PATENT DOCUMENTS 4,813,060  3/1989  Heubeck et al. .

Primary Examiner—Craig E. Church
Attorney, Agent, or Firm—Andrus, Sceales, Starke & Sawall

[57] ABSTRACT

An exposure apparatus for panoramic x-ray equipment automatically adjusts imaging parameters. The intensity of radiation passed through the patient is measured by detectors, such as photo diodes, and provided to a control unit. On the basis of the measured radiation, the control units identifies anatomical features and adjusts the imaging parameters accordingly.

13 Claims, 2 Drawing Sheets

AUTOMATIC EXPOSURE APPARATUS FOR PANORAMIC X-RAY EQUIPMENT

This is a continuation-in-part application of U.S. patent application Ser. No. 07/931,834, filed on Aug. 18, 1992 also by Erkki Jarvinen, now abandoned.

The present invention relates to an automatic exposure control for panoramic x-ray equipment capable of producing correctly exposed panoramic x-ray images, regardless of the anatomy and dental structure of a patient. This is accomplished by utilizing the dependence of the intensity of the radiation passed through a patient upon the anatomy of a patient in controlling the generation of the x-ray image. In particular, this is accomplished by using radiation information to identify certain locations on a patient's jawbone, measuring the radiation absorption characteristics, i.e. bone thickness, at such locations, and using such identification and/or measurements to control imaging parameters.

Prior art automatic exposure apparatus for panoramic x-ray equipment determine imaging parameters, (e.g. kV and mA of an x-ray tube, rotating speed of film advancement or of a boom supporting the x-ray tube and film cassette) by measuring the radiation passed through a patient either on the basis of a single sample taken at a given imaging moment or by continuously measuring.

In U.S. Pat. No. 4,813,060, a system is disclosed wherein exposure data is measured as x-rays transilluminate in a space between a patient's neck vertebrae and a patient's jawbone (i.e. between the vertebrae and ramus of the mandibula), and then imaging parameters such as tube voltage Kv, tube current Ma, or film speed can be adjusted in accordance with the measured data taken while the x-rays pass through the space.

A drawback in the prior art techniques is that the adjustment of imaging parameters does not take into account differences in the anatomies of patients. Thus, an irregularity in the dental structure of the patient may ruin the imaging result. The adjustment effected on the basis of a single sample is particularly sensitive to errors since irregularities may be imaged right within the area of a sample; such as styloid process, hyoid bone, vertebrae of the neck, shadows of dental fillings or the like.

Continuously controlled automatic exposure apparatus is also sensitive to errors. In particular, the vertebrae of the neck constitutes a problem for continuous adjustment. If adjustment is fast, the vertebrae are exposed correctly, but the image contains disturbing streaks. If adjustment is too slow, the beginning portion of the neck is too light and the end portion is too dark. Also, amalgam fillings appearing in the dental area or some missing teeth can cause exposure errors.

There are also various prior art ways estimating the equivalent thickness of the cranium (e.g. on the basis of a patient's weight, cranial diameter or the like secondary dimensions), and using the estimated equivalent thickness of the cranium for exposure control. A drawback in these methods is that individual secondary dimensions of the cranium do not correlate exceptionally well with equivalent cranial thickness. Rather, correlation is statistical and exceptions are major and usual. The equivalent cranial thickness is, in fact, affected by a plurality of factors, such as e.g. the size, the sex, and particularly the age (osteoporosis phenomenon), as well as the racial features, of the patient.

An advantage offered by the present invention is that the selection of imaging parameters (i.e. kV, mA, speed of imaging movements) can be effected on the basis of a reliable measurement. This advantage is achieved by measuring the intensity of radiation passed through a patient at a desired location (preferably the ramus of the mandibula), and adjusting imaging parameters in response to the intensity measurement made at the desired location. In its preferred embodiment, the invention is particularly effective because the density of the ramus of the mandibula is typically the same as the average density of the roots of a patient's teeth, and the roots of the teeth contain the most important information of an image for a dentist.

Figure 2:
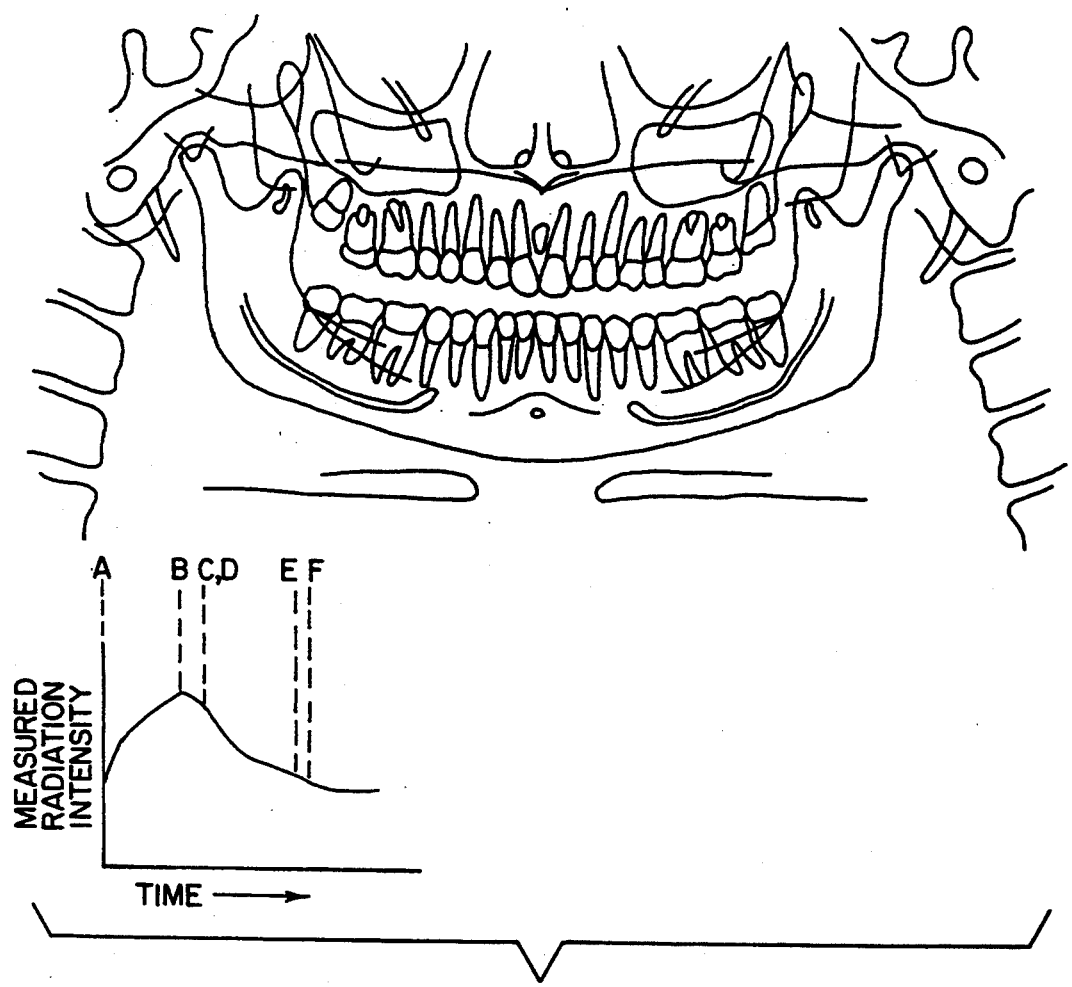

The invention will now be described in more detail with reference made to the accompanying drawing in which:

FIG. 1 illustrates schematically an imaging system incorporating the apparatus of the invention; and FIG. 2 shows a panoramic x-ray image, and a plot of an exemplary radiation response of a detector in accordance with the present invention.

Behind the imaging instrument of a panoramic x-ray equipment, as shown in FIG. 1, e.g. a film cassette 1, is located one or a plurality of detectors 2, e.g. a photo diode for measuring x-ray radiation. The output signals of detectors 2 are amplified by an amplifier 3 and the amplified signal at 4 is carried to a control unit 5. Control unit 5 may comprise a microprocessor or programmable logic unit which is capable of carrying out appropriate signal processing to provide a desired output. As shown in the graph of FIG. 2, control unit 5 is specifically capable of analyzing an image from the measured values of radiation intensity passing through the patient provided by detector 2 and amplifier 3 as the imaging process proceeds.

The measured values of radiation intensity are sampled at short (e.g 50–100 ms) intervals and from the changes and rate of change of measured values, as determined by control unit 5, identification of anatomy appearing in the image is effected as a primitive outline identification utilizing known features appearing in the panoramic x-ray images. To start an image, measured values of radiation intensity are used to directly ascertain when the cervical column appears at the beginning of the scan (point A in FIG. 2). An interface between a soft tissue and bone tissues (e.g. the edge of the mandibula in the marginal portions of an image) is also ascertained.

FIG. 2 shows a plot of an exemplary radiation response of detectors 2 compared to a panoramic x-ray image. In particular, the curve in FIG. 2 shows how measured radiation intensity typically varies over time as imaging begins. The imaging proceeds in the direction of the arrow in FIG. 2. The start of the exposure is marked by A in the plot, the maximum response is marked by B, the edge of the ramus of the mandibula is marked by C, a measurement region is marked by D and E, and the "nominal" start of the teeth is marked by F.

By identifying the edge C of the ramus, signal data obtained from the ramus, i.e. the region D-E, can be used to determine the radiation absorption characteristics of the jaw for adjusting imaging parameters. The density of the ramus is typically the same as the average density of the roots of the teeth, and the roots of the teeth contain the most important information of the panoramic x-ray image to the dentist. Therefore, by adjusting the imaging parameters to correctly image the ramus area, the remainder of the image will also be correctly adjusted.

The edge C of the ramus of the mandibula may be identified and adjustment of the imaging parameters in the ramus area from points D to E may be carried out in the following manner.

(1) As the imaging process commences and proceeds, the peak response of the detector 2 is detected (i.e. at point B). Note that the peak B is a characteristic value that can be used to identify an area just prior to the edge of the ramus of the mandibula. In other circumstances, a characteristic value need not be a peak but rather some other characteristic that can be readily determined.

(2) The peak (i.e. point B) of average reference data is matched to the detected peak, in time scale. That is, the distance along the time axis between points A and B should match for both the average reference data and the measured data. The average reference data is stored in control unit 5 and may be understood as data that would produce the image of a typical or "normal" jaw.

(3) The output of detectors 2 is measured as the imaging of the ramus proceeds, i.e. in the region D-E in FIG. 2. As noted above, this is preferably carried out on a sampling basis. In the normal case, region D-E is determined by a fixed time period (e.g. 1-2 secs). Thus, the duration of region D-E is typically constant among patient, whereas the time between the end of the adjustment E and the "nominal" start of the teeth F varies. Depending on the timing of the peak value B, the duration of region D-E may be limited by a maximum time period for scanning from points A-E (e.g. 2-3 secs). This is so that adjustment will terminate before point F, even if peak value B is detected after an unusually long period of time. If peak value B is not detected after an unusually long period of time (e.g. 1-2 secs), adjustment can be triggered to automatically begin at that time so that adjustment is completed before point F.

(4) Imaging parameters (for example, tube voltage kV, tube current mA, or speed of image movement) in the ramus area are adjusted according to the detector output signal in conductor 4. This adjustment can be accomplished as follows:
  (a) the actual detector output signal is compared to the reference data, which is the expected response in a particular location. Differences between the actual signal data and the reference data are due to the radiation absorption characteristics of the particular patient jaw being imaged, primarily bone thickness and/or density. It will also be dependent on properties of the panoramic x-ray equipment. In addition to factors such as voltage and current, the detector output will be affected by offsets or bias entered in the equipment for film sensitivity, film processing factors, and the like.
  (b) the imaging parameters are increased or decreased until the response of the detector 2 correlates to the reference value in each location of the image.

(5) based on the amount of correction needed in step (b) the amount of adjustments of the imaging parameters to obtain proper exposure of the teeth is determined and applied to the equipment.

(6) imaging of the jaw then proceeds.

To enhance the accuracy of the reference data representing a typical or normal jaw, the reference data can be altered based on the actual data obtained from each actual imaging procedure. For example and in the simplest form, once a statistically significant number of procedures have been carried out, the reference data may comprise the average of the actual values obtained in the procedures. The data from each successive imaging procedure is then included in the average so that its accuracy as an indication of the radiation absorption properties of a typical human jaw continues to improve.

Referring again to FIG. 1, with the adjustment of the imaging parameters in the above described manner, the control unit 5 regulates the film exposure in a manner that reference values of the tube voltage and/or tube current of x-ray tube 9 are varied by means of a differential amplifier included in the control loop of an x-ray generator 6. In addition to, or in place of, the foregoing, the speeds of imaging movements may be regulated accordingly by changing the imaging movement control elements, e.g. the operating frequency of stepping motors 7.

Thus, an x-ray apparatus of the invention is provided with detectors 2 for measuring at certain locations the radiation 8 passed through a patient 10. An amplifier 3 provides an amplified output signal in conductor 4. The apparatus also has means 5, 6 and 7 for regulating the imaging parameters, such as tube voltage kV, tube current mA, and the speeds of imaging movements.

The imaging apparatus of the invention can be preferably used in a manner that, prior to the actual adjustment of imaging parameters, an examination is made to determine whether the cervical vertebrae have been imaged by the imaging instrument. This can be followed by effecting a rough adjustment of imaging parameters after a beam of rays 8 has moved beyond the cervical vertebrae but before the beam 8 has reached the edge of the ramus of the mandibula. Such a rough adjustment should then be followed by fine adjustment, which occurs as the beam 8 moves through the ramus of the mandibula as described above.

I claim:

1. In panoramic x-ray equipment having an x-ray radiation source and a film cassette that move relative to a jaw region of a patient during a panoramic imaging process in which film exposure depends on imaging parameters in the panoramic x-ray equipment, an improvement comprising an automatic exposure apparatus having:
  an x-ray radiation detector for ascertaining the intensity of radiation passing through the jaw region of the patient in the imaging process and providing an output signal corresponding to the same; and
  a control means coupled to the detector for analyzing the detector output signal and identifying the imaging of a ramus of a mandibula of the patient's jaw, the control means adjusting the imaging parameters at least once during the imaging process in accordance with the radiation intensity ascertained from the imaging of the ramus.

2. The apparatus as set forth in claim 1 wherein the control means analyzes the detector output signal to identify an edge of the mandibula of the patient and adjusts the imaging parameters in accordance with the radiation intensity ascertained from the imaging of the ramus of the mandibula.

3. The apparatus as set forth in claim 2 wherein the control means adjusts the imaging parameters to desired values after the ramus of the mandibula has been imaged.

4. The apparatus as set forth in claim 1 wherein the control means further analyzes the detector output signal for absence of cervical vertebrae imaging and roughly adjusts the imaging parameters in such absence.

5. The apparatus as set forth in claim 2 wherein the control means further analyzes the detector output signals for absence of cervical vertebrae imaging and roughly adjust the imaging parameters in such absence.

6. The apparatus as set forth in claim 3 wherein the control means further analyzes the detector output signal for absence of cervical vertebrae imaging and roughly adjusts the imaging parameters in such absence.

7. The apparatus as set forth in claim 1 wherein the x-ray radiation detector includes a photo diode.

8. The apparatus as set forth in claim 1, further including an amplifier for amplifying the output signal of the detector.

9. A method for adjusting imaging parameters when creating a panoramic tomographic image, the method comprising the steps of:

passing a beam of x-radiation through a patient's jaw region and moving the beam panoramically around the patient's jaw region to image a patient's jaw;

detecting the radiation intensity of the beam as the beam moves around the patient;

determining a characteristic value in the radiation intensity data to allow the identification of a ramus of a mandibula of the patient's jaw;

comparing the radiation intensity data to reference data for the ramus;

altering imaging parameters so that the detected radiation intensity correlates to the reference data; and, adjusting the imaging parameters to be used for imaging the patient's jaw as the beam moves panoramically around the patient's jaw in accordance with the correlating alteration.

10. A method as recited in claim 9 further comprising the step of:

roughly adjusting the imaging parameters in response to radiation intensity delta detected in time before the imaging of the ramus.

11. A method as recited in claim 9 wherein the beam is moved panoramically from beyond the ramus of the mandibula and through the ramus to adjust imaging parameters before imaging the remaining portions of the jaw region with altered imaging parameters.

12. A method as recited in claim 11 further comprising the step of:

roughly adjusting the imaging parameters in response to radiation data detected before the beam reaches the edge of the ramus of the mandibula.

13. A methods as recited in claim 9 further comprising the step of:

adjusting the reference data following the imaging procedure in accordance with the radiation intensity data obtained during the imaging procedure.

* * * * *